(12) United States Patent
Schwebel et al.

(10) Patent No.: US 11,844,782 B2
(45) Date of Patent: Dec. 19, 2023

(54) AQUEOUS COMPOSITION COMPRISING DANTROLENE

(71) Applicant: SPEPHARM AG, Lucerne (CH)

(72) Inventors: Hervé Jean Schwebel, Mulhouse (FR); Vincent Adamo, Marly (CH)

(73) Assignee: SPEPHARM AG, Lucerne (CH)

( * ) Notice: Subject to any disclaimer, the term of this patent is extended or adjusted under 35 U.S.C. 154(b) by 360 days.

(21) Appl. No.: 15/952,477

(22) PCT Filed: Oct. 19, 2016

(86) PCT No.: PCT/EP2016/075086
§ 371 (c)(1),
(2) Date: Apr. 13, 2018

(87) PCT Pub. No.: WO2017/067980
PCT Pub. Date: Apr. 27, 2017

(65) Prior Publication Data
US 2018/0256548 A1 Sep. 13, 2018

(30) Foreign Application Priority Data

Oct. 20, 2015 (EP) .................................... 15190601
Jun. 17, 2016 (EP) .................................... 16174999

(51) Int. Cl.
| | | |
|---|---|---|
| *A61K 31/277* | (2006.01) | |
| *A61K 31/4178* | (2006.01) | |
| *A61K 9/08* | (2006.01) | |
| *A61K 47/40* | (2006.01) | |

(52) U.S. Cl.
CPC ............ *A61K 31/4178* (2013.01); *A61K 9/08* (2013.01); *A61K 47/40* (2013.01)

(58) Field of Classification Search
CPC ...... A61K 31/4178; A61K 47/40; A61K 9/08; A61P 21/02
USPC ........................................................ 514/390
See application file for complete search history.

(56) References Cited

U.S. PATENT DOCUMENTS

| | | | | |
|---|---|---|---|---|
| 6,407,079 | B1 * | 6/2002 | Muller ................. | A61K 9/0019 514/58 |
| 8,975,284 | B2 * | 3/2015 | Malkawi ................... | A61P 9/06 514/341 |
| 9,138,407 | B2 | 9/2015 | Caponetti et al. | |
| 2008/0260848 | A1 * | 10/2008 | Nagata ................. | A61K 9/0043 424/499 |
| 2009/0036406 | A1 | 2/2009 | Nakai et al. | |
| 2009/0163574 | A1 | 6/2009 | Kim et al. | |
| 2014/0099382 | A1 | 4/2014 | Anderson et al. | |

FOREIGN PATENT DOCUMENTS

| | | |
|---|---|---|
| EP | 2583670 A1 | 4/2013 |
| JP | S5320413 A | 2/1978 |
| JP | H062G3636 A | 9/1994 |
| JP | 2003321364 A | 11/2003 |
| JP | 2006199588 A | 8/2006 |
| JP | 2009538294 A | 11/2009 |
| RU | 2497507 C2 | 11/2013 |
| WO | 9962958 A1 | 12/1999 |
| WO | 2006134877 A1 | 12/2006 |
| WO | 2009104080 A2 | 8/2009 |
| WO | 2010126818 A1 | 11/2010 |

OTHER PUBLICATIONS

Uekama, K., "Design and Evaluation of Cyclodextrin-Based Drug Formulation," 2004, pp. 900-915, vol. 52, No. 8, Chemical and Pharmaceutical Bulletin, 2004 Pharmaceutical Society of Japan.
International Search Report and Written Opinion for International Application No. PCT/EP2016/075086, dated Jan. 10, 2017—9 pages.
Khan et al., "Stability Characterization, Kinetics and Mechanism of Degradation of Dantrolene in Aqueous Solution: Effect of pH at Temperature", Pharmacology & Pharmacy, 2012, 3, pp. 281-290.
Rasheed et al., "Cyclodextrins as Drug Carrier Molecule: A Review", Scienticia Pharmaceutica, vol. 76, No. 4, Jan. 1, 2008 (Jan. 1, 2008), pp. 567-598.
Jansen et al: "Some physical-chemical properties of dantrolene and two of its analogues", International Journal of Pharmaceutics, Elsevier BV, NL, vol. 75. No. 2-3, Sep. 20, 1991 (Sep. 20, 1991), pp. 193-199.
Japanese Office Action received in Application No. 2018-520391 dated Sep. 1, 2020, 5 pages.
Guangjie, "Pharmaceutical Excipient Application Technology," Pharmaceutical Preparation Research Room of Shanghai Pharmaceutical Industry Research Institute, China Medical Science and Technology Press, Dec. 1991, 3 pages.
Office Action received in Chinese Application No. 201680061801.6 dated Mar. 26, 2021, with translation, 21 pages.
Koki Wada Research Institute; "Characteristics and Uses of Cyclodextrin Derivatives: Focusing on Hydroxypropyl-β-Cyclodextrin." (2011); Bulletin of Applied Glycoscience, vol. 1, p. 322-326.
Fuchs, Holger, et al. "Brain penetration of WEB 2086 (Apafant) and dantrolene in Mdr1a (P-glycoprotein) and Bcrp knockout rats." Drug Metabolism and Disposition 42.10 (2014): 1761-1765.
Jansen, A. C. A., et al. "The influence of inclusion by cyclodextrins on absorption kinetics of dantrolene in the rat." Proceedings of the Fourth International Symposium on Cyclodextrins: Munich, West Germany, Apr. 20-22, 1988. Springer Netherlands, 1988.
JPO; App. No. JP 2018-520391; Office Action dated Nov. 26, 2021; "Report of pretrial examination".
Poelma, FGJ, et al. "The Effect of Inclusion in Cyclodextrins on the Absorption of Dantrolene." Pharmaceutisch Weekblad-Scientific Edition, vol. 10. No. 6.; Royal Dutch Assoc Advancement Pharmacy, 1988.

(Continued)

*Primary Examiner* — Layla Soroush
(74) *Attorney, Agent, or Firm* — BakerHostetler; Toni-Junell Herbet (57) ABSTRACT

An aqueous composition includes either dantrolene or a pharmaceutically acceptable salt thereof and a cyclodextrin derivative, with the pH of the aqueous composition greater than 7. A powder can be obtained by drying the composition. The powder can be included in a kit.

31 Claims, 6 Drawing Sheets

(56) References Cited

OTHER PUBLICATIONS

Poelma, FGJ, et al. "Intestinal absorption of drugs II. The effect of inclusion in cyclodextrins on the absorption of dantrolene." Journal of inclusion phenomena and molecular recognition in chemistry 7 (1989): 423-430.
Roquette; Hydroxypropyl Beta-cyclodextrin, "An Enabling Technology for Challenging Pharmaceutical Formulations"; May/Jun. 2009.
Tomonaga, F., et al. "Pharmaceutical studies of dantrolene sodium." Hiroshima J Anesthesia 15.Suppl (1979): 101-8.
Loftsson et al., "Pharmaceutical Applications of Cyclodextrins. 1. Drug Solubilization and Stabilization", Journal of Pharmaceutical Sciences, vol. 85, No. 10, Oct. 1996, pp. 1017-1025.
"Pharmaceutical Dosage Forms", Pharmaceutics Devision of Korean Association of Pharmacy Education, 1995, with English translation.
Dykes, "Evaluation of a muscle relaxant: dantrolene sodium (Dantrium)", JAMA, vol. 231(8), Feb. 24, 1975 (Abstract).

\* cited by examiner

AQUEOUS COMPOSITION COMPRISING DANTROLENE

RELATED APPLICATIONS

This application is the United States National Phase entry of International Application No. PCT/EP2016/075086, filed Oct. 19, 2016, which claims the benefit of priority of European Application No. 16174999.9, filed Jun. 17, 2016, and of European Application No. 15190601.3, filed Oct. 20, 2015. The contents of International Application No. PCT/EP2016/075086, European Application No. 16174999.9 and European Application No. 15190601.3 are incorporated by reference herein in their entireties.

FIELD

The present disclosure relates to an aqueous composition comprising dantrolene or a pharmaceutically-acceptable salt thereof and a cyclodextrin derivative wherein the pH of the aqueous composition is greater than 7. Further, the present disclosure relates to a powder obtained by drying the composition of the disclosure as well as a kit comprising said powder.

BACKGROUND

Malignant hyperthermia is a life-threatening genetic sensitivity of skeletal muscles to volatile anesthetics and depolarizing neuromuscular-blocking drugs used for general anesthesia. In susceptible individuals, these drugs can induce a drastic and uncontrolled increase in skeletal oxidative metabolism, which overwhelms the body's capacity to supply oxygen, remove carbon dioxide and regulate body temperature, eventually leading to circulatory collapse and death if not treated quickly.

The current treatment of choice for malignant hyperthermia is the administration of dantrolene, a hydantoin derivative first described in 1967. Dantrolene is a postsynaptic muscle relaxant which lessens the excitation-contraction coupling in muscle cells. However, dantrolene is poorly soluble in water, leading to formulations which exhibit a number of undesirable properties. These problems include cumbersome and, at times, imprecise preparation, the investment of significant time and the employment of elevated temperatures in the preparation of solutions suitable for intravenous administration and the necessity to administer large volumes of solution in order to deliver an efficacious dose, typically ranging from 2.5 to 10 mg/kg body weight. The poor solubility in water also extends to the pharmaceutically-acceptable salts of dantrolene which in solution over time, precipitate in the form of the free acid. The resultant mixtures are unacceptable for injection. The short shelf-life of the solution has been addressed in the art by keeping a powder at hand which has been obtained by freeze-drying the dantrolene solution. However, the final administration of the formulation generally involves reconstitution of this powder into an injectable liquid which typically, and preferably, involves dissolving the powder in an aqueous diluent. Therefore, there remains a need to provide storage-stable and parenterally-injectable formulations of dantrolene and its salts which exhibit increased solubility in the preferred aqueous preparations and to provide injectable liquids which allow the effective administration of an efficacious dose of dantrolene.

EP 2 583 670 provides methods of using tert-butyl alcohol (TBA) co-solvent systems in the formulation and production of a pharmaceutical agent with low solubility, in particular a method of making dantrolene sodium formulation for intravenous use.

US 2014/0099382 provides low-volume formulations of dantrolene which are safe for injection and which comprise dantrolene sodium, a water-soluble polysorbate, sorbitol or mannitol, and water as a liquid carrier, wherein said dantrolene sodium and water are present together as a colloidal dispersion of dantrolene sodium particles in water.

U.S. Pat. No. 6,407,079 refers to pharmaceutical compositions comprising inclusion compounds of sparingly-water-soluble or water-instable drugs with β-cyclodextrin ethers or β-cyclodextrin esters and processes for the preparation thereof.

WO 99/62958 refers to cyclodextrin derivatives having at least one lower alkyl group and at least one $C_{2-20}$ alkanoyl group in the molecule, which are suitable to closely compound a medicament.

Cyclodextrins may be used to enhance the solubility, stability and bioavailability of drugs. Although commonly known for their stabilizing effect, cyclodextrins can also have a destabilizing effect on drugs through direct catalysis. The catalytic effect is associated with deprotonation of the hydroxyl groups located at the rim of the cyclodextrin cavity. This catalytic effect is mainly observed under basic conditions and increases with increasing pH (A. Raheed et al, *Cyclodextrins as Drug Carrier Molecule: A Review*, Scientia Pharmaceutica 2008, 76, 567-598).

Further, it is known that dantrolene undergoes hydrolysis in alkaline solutions causing it to degrade via hydantoin ring opening to form a ring-opened compound. The degradation is accelerated with increasing pH value and is enhanced at elevated temperatures. Studies show that the specific base catalysis becomes more prominent as the pH increases from 7.5 to 9.5 thus resulting in an increase in the degradation rate of dantrolene (S. R. Khan et al, *Stability Characterization, Kinetics and Mechanism of Degradation of Dantrolene in Aqueous Solution: Effect of pH at Temperature, Pharmacology & Pharmacy*, 2012, 3, 281-290).

In WO 2010/126818 A1 compositions in which an excess of dantrolene is mixed with a lesser amount of cyclodextrine derivative to provide heterogeneous pastes are disclosed. Jansen et al: "Some physical-chemical properties of dantrolene and two of its analogues", International Journal of Pharmaceutics, Elsevier BV, NL, vol. 75. No. 2-3, 20 Sep. 1991 (1991 Sep. 20), pages 193-199 discloses the possibility to mix dantrolene with cyclodextrine in a molar ratio of 1:100 to 1:1000.

As further art U.S. Pat. No. 6,407,079 B1; and Rasheed et al: "Cyclodextrins as Drug Carrier Molecule: A Review", Scienticia Pharmaceutica, vol. 76, no. 4, 1 Jan. 2008 (2008 Jan. 1), pages 567-598 can be mentioned.

Due to the severity of the effects of malignant hyperthermia, every hospital is advised to keep dantrolene in stock and, thus, every hospital is confronted with the above-described problems. Therefore, there still exists a need for dantrolene solutions which are easy to prepare and which exhibit acceptable stability over an extended period of time.

SUMMARY

It is therefore an object of the present disclosure to provide an aqueous composition comprising either dantrolene or a pharmaceutically acceptable salt thereof which exhibits an increased storage stability and increased solubility in aqueous liquid formulations.

It is a further object of the present disclosure to provide compositions, especially powders, comprising either dantrolene or a pharmaceutically acceptable salt thereof which can be reconstituted fast and easily to clear solutions.

During the development of the present disclosure, it was surprisingly found that, in contrast to the teachings of the prior art, increased storage- and chemical-stability as well as increased solubility could be achieved for aqueous compositions comprising either dantrolene or a pharmaceutically acceptable salt thereof together with a cyclodextrin derivative at alkaline pH values.

An embodiment of the present disclosure is an aqueous composition comprising
i) Component (A) selected from one or more members of the group consisting of dantrolene and a pharmaceutically acceptable salt of dantrolene; and
ii) Component (B) selected from one or more members of the group consisting of cyclodextrin derivatives,
wherein the pH of the composition is greater than 7, and
wherein the molar ratio of component (A) to component (B) ranges from 1:2 to 1:30, preferably 1:3 to 1:30.

The aqueous composition is preferably liquid at 20° C.

Throughout the description the values and parameters referred to are determined at 20° C. unless stated otherwise.

Component (A)

Component (A) is an essential component of the aqueous composition of the present disclosure.

Component (A) is selected from the group consisting of dantrolene and a pharmaceutically acceptable salt thereof.

Component (A) can be represented by the following formula (I), wherein formula (I) represents dantrolene:

A pharmaceutically acceptable salt of dantrolene refers to a deprotonated form of dantrolene and a cationic counter ion $X^+$. The cationic counter ion $X^+$ is preferably selected from the group of alkaline metal, earth alkaline metal, ammonium, alkyl-ammonium, polyalkyl-ammonium, aryl-ammonium, substituted or unsubstituted quinolizinium and substituted or unsubstituted pyridinium.

The pharmaceutically acceptable salt of dantrolene refers to a salt of dantrolene in which the cationic counter ion $X^+$ to the dantrolene anion is preferably selected from the group consisting of sodium, potassium, ammonium, calcium, magnesium, the ammonium salts of physiologically acceptable amino compounds, especially selected from the group consisting of arginine, lysine, meglumine, tromethamine; choline, benzyltrimethylammonium, tetramethylammonium, N-methylpyridinium, tetrabutylammonium, 2-(2,3-dihydroxy-1-proylamino)-quinolizinium, quinolizinium, 2-carbonyl-1-methylpyridinium, 2,3-dimethyl-1-phenyl-4-trimethyl-ammonium-3-pyrazolin-5-one, dimethylammonium, 1,3-dimethylimidazolium and 2-(1-hydroxy-2-methyl)propyltri-methylammonium.

In a preferred embodiment, the counter ion $X^+$ to the dantrolene anion is selected from the group consisting of sodium, potassium, ammonium, calcium and magnesium. In an especially preferred embodiment, the counter ion $X^+$ to the dantrolene anion is sodium.

It has been surprisingly found that the stability of component (A) in the composition of the disclosure could be increased by increasing the pH of the composition. Therefore, in a preferred embodiment of the composition, the pH ranges from 7.5 to 10.5, preferably from 8.0 to 10.0, more preferably from 8.5 to 9.5.

In a preferred embodiment, component (A) is present in the composition of the disclosure in a concentration ranging from 0.1 to 10 mg/ml, preferably from 0.2 to 7.0 mg/ml, especially from 0.3 to 6.0 mg/ml, based on the volume of the aqueous composition.

In a further aspect of the disclosure the aqueous composition of the disclosure comprises component (A) in a concentration ranging from 0.25 to 25.0 mmol/l, more preferably from 0.50 to 17.50 mmol/l and especially from 0.75 mmol/l to 15.0 mmol/l, based on the volume of the aqueous composition.

Component (B)

A further essential component of the aqueous composition of the disclosure is component (B).

Component (B) is selected from the group consisting of cyclodextrins and cyclodextrin derivatives.

Cyclodextrins are cyclic (α-1,4)-linked oligosaccharides possessing a hydrophobic central cavity and a hydrophilic outer surface. Due to their truncated cone or torus, cyclodextrins may interact with appropriately-sized molecules to give rise to the formation of inclusion complexes. Examples of suitable cyclodextrins are β-cyclodextrin or γ-cyclodextrin.

It has been surprisingly found that the water solubility of component (A) can be increased by the introduction of substituents to component (B). In a preferred embodiment, component (B) is a derivative of a cyclodextrin, preferably a cyclodextrin (preferably a β-cyclodextrin), which comprises one or more substituents, selected independently and preferably from the group consisting of alkyl, hydroxyalkyl, carboxyalkyl, alkylcarbonyl, carboxyalkoxyalkyl, sulfoalkyl, alkylcarbonyloxyalkyl, alkoxycarbonylalkyl and hydroxyl-(mono or poly)alkyl groups.

In the foregoing, the terms "alkyl" and "alkylene" are to be understood to include both straight- and branched-hydrocarbon radicals which may or may not be substituted.

Preferably, each alkyl or alkylene moiety contains up to 6 carbon atoms, preferably from 1 to 6 carbon atoms, more preferably from 2 to 4 carbon atoms, especially 3 or 4 carbon atoms.

Sulfoalkyl refers preferably to a —$C_{1-10}$-alkyl-$SO_3H$ moiety or a corresponding pharmaceutically-acceptable salt thereof. Preferred counter ions are those which are defined as the counter ion $X^+$ for component (A) above.

In a preferred embodiment, component (B) is selected from β-cyclodextrin and β-cyclodextrin derivatives.

Further preferred is an embodiment of the present disclosure wherein component (B) is selected from the group consisting of β-cyclodextrin, 2,6-dimethyl-β-cyclodextrin, 2-hydroxyethyl-β-cyclodextrin, 2-hydroxyethyl-γ-cyclodextrin, 2-hydroxypropyl-γ-cyclodextrin, (2-carboxymethoxy)propyl-β-cyclodextrin, sulfonylbutyl-β-cyclodextrin and 2-hydroxypropyl-β-cyclodextrin.

In a preferred embodiment, component (B) is represented by formula (II)

II wherein one or more of substituents R is/are independently selected from the group consisting of H, alkyl, hydroxyalkyl, carboxyalkyl, alkylcarbonyl, carboxyalkoxyalkyl, —$C_{1-10}$-alkyl-$SO_3H$ or a corresponding pharmaceutically acceptable salt thereof, alkylcarbonyloxyalkyl, alkoxycarbonylalkyl and hydroxyl-(mono or poly)alkyl.

Preferably, each alkyl or alkylene moiety contains up to 10 carbon atoms, more preferably from 1 to 6 carbon atoms, even more preferably from 2 to 4 carbon atoms, especially 3 or 4 carbons.

In a preferred embodiment, one or more of the substituents R are selected from the group consisting of H, —$CH_2CH(CH_3)OH$, —$(CH_2)_4SO_3Na$, —$CH_3$, glucosyl, hydroxyethyl and maltosyl.

In an especially preferred embodiment, component (B) is selected from the group consisting of 2-hydroxypropyl-β-cyclodextrin, sulfobutylether-β-cyclodextrin sodium salt and 2-hydroxyethyl-β-cylodextrin. In an especially preferred embodiment, component (B) is 2-hydroxypropyl-β-cyclodextrin.

The best results are achieved if component (B) is a cyclodextrin, preferably a β-cyclodextrin, having a molar substitution (MS) ranging from 0.05 to 10. Therefore, an embodiment of the present disclosure is preferred wherein component (B) is a cyclodextrin having an average molar substitution ranging from 0.05 to 10, preferably from 0.2 to 2, especially from 0.25 to 1 and in particular from 0.5 to 0.8. The average molar substitution is generally used as a measure of the average number of moles of all substituents per glucose unit.

In an especially preferred embodiment, component (B) is 2-hydroxypropyl-β-cyclodextrin having a molar substitution of 0.2 to 0.9, preferably 0.3 to 0.8, especially 0.5 to 0.7.

Preferably, the aqueous composition of the disclosure comprises component (B) in a concentration ranging from 15 to 400 mg/ml, preferably from 20 to 350 mg/ml, especially from 50 to 300 mg/ml, based on the volume of the aqueous composition.

In one aspect of the disclosure the aqueous composition comprises component (B) in a concentration ranging from 10 to 300 mmol/l, preferably from 14 to 250 mmol/l and especially from 36 to 210 mmol/l, based on the total volume of the aqueous composition.

In developing the present disclosure, a careful balance was established between the quantity of component (A) and that of component (B) in the aqueous composition of the disclosure. The best results with regard to the stability of component (A) were achieved when the molar amount of component (B) was higher than that of component (A) with the molar ratio of (A):(B) being from 1:2 to 1:30, preferably 1:3 to 1:30.

Therefore, further preferred is an embodiment of the present disclosure wherein the molar ratio of component (A) to component (B) ranges from 1:5 to 1:18.

Preferably, the weight ratio of component (A) to component (B) in the composition of the disclosure ranges from 1:10 to 1:100, preferably from 1:17 to 1:65. However, in preferred embodiments, in case of discrepancy, as throughout the entire description for any discrepancies with the molar ratio, the molar ratio takes precedence, i.e. the weight ratio (or other value) has to be varied such that the molar ratio is met.

The aqueous composition according to the disclosure has a pH which is higher than 7. In order to adjust the pH value to the desired range and to compensate for the acidity of possible diluents, pH adjuster may be used. Therefore, in a preferred embodiment, the aqueous composition further comprises a pH adjuster. pH adjusters within the meaning of the present disclosure are compounds or systems which are capable of adjusting and maintaining the pH of the aqueous composition according to the disclosure within a specific range, e.g. higher than 7, preferably from 7.5 to 10.5, more preferably from 8.0 to 10.0, especially preferred from 8.5 to 9.5.

In a preferred embodiment, the pH adjuster is selected from the group consisting of citrate, carbonate, phosphate, arginine, lysine, meglumine, tromethamine, histidine and mixtures thereof.

The pH adjuster may be used as a pH buffer or as a part of a pH buffering system.

In a preferred embodiment, the pH adjuster is present in the inventive composition in an amount suitable to adjust and maintain the pH of the composition within an alkaline range. Preferably, the amount of the pH adjuster in the composition is chosen in relation to the amount of component (A) present in the inventive composition. In a preferred embodiment, the molar ratio of component (A) to pH adjuster ranges from 20:1 to 1:20, preferably from 10:1 to 1:10, especially preferred from 8:1 to 1:5.

The aqueous composition of the disclosure comprises an aqueous diluent. Preferably, the diluent is water or a mixture of water with physiologically-tolerable solvents. Usually the amount of water is higher than 50 wt.-%, preferably higher than 75 wt.-%, especially higher than 95 wt.-%, based on the total amount of diluent. In one aspect of the disclosure, the weight ratio of water to organic solvents in the aqueous diluents is at least 1:2, preferably at least 1:1, more preferably at least 2:1, especially at least 5:1 or at least 10:1, in particular at least 20:1 or at least 50:1. In a further aspect of the disclosure, the diluent comprises at least 0.5 weight-% (wt.-%), preferably at least 1.0 wt.-%, more preferably at least 5 wt.-%, especially from 0.5 to 30 wt.-% of organic solvents, wherein the quantities are based on the total weight of diluents. Suitable diluents for the aqueous composition are defined hereinafter.

As is known to the person skilled in the art, the problem of short storage life of aqueous compositions comprising a dantrolene compound has been addressed by drying the aqueous composition and storing the obtained powder until reconstitution immediately prior to use. However, these powders generally suffer from poor solubility and require the use of large amounts of solvents such to render them suitable for injection. It is a further object of the disclosure to provide a formulation of dantrolene, especially a dantrolene salt such as the sodium salt of dantrolene, that are rapidly and reliably reconstituted in emergency clinical situations as well as in non-emergency and prophylactic circumstances. In particular, the formulation will be such that a full therapeutic dose of 300 mg or 200 mg of the sodium salt of dantrolene can be reconstituted in a clinical situation in less than 1 minute by a single clinician. It has surprisingly been found that a powder which is obtained by drying the inventive composition readily dissolves in water or an appropriate aqueous diluent.

A further embodiment of the present disclosure is therefore a powder which is obtainable by drying the aqueous composition of the disclosure. The aqueous composition of the disclosure may be dried by any suitable means known to the person skilled in the art. In a preferred embodiment, the powder of the disclosure is obtained by lyophilization of the aqueous composition of the disclosure. In a preferred embodiment, the powder of the disclosure is an instant powder, i.e. a powder which instantly dissolves in water. In this context, instantly dissolves is to be understood to mean that 100% of the powder dissolves within 30 seconds upon stirring at 20° C.

As discussed above, the key step in the treatment of malignant hyperthermia is the immediate administration of the dantrolene compound. The dantrolene compound should therefore be readily available in an administrable form, preferably in a form suitable for injection. Further, laborious mixing of the components should be avoided such to, on the one hand, save time and, on the other hand, to avoid potential hazards to both the patient and the staff that may be caused by mishandling of the components.

A further object of the present disclosure is a kit which allows fast and accurate preparation of the composition of the disclosure.

The kit according to the disclosure comprises at least one first compartment, which comprises the powder of the disclosure, and at least one second compartment, which comprises an aqueous diluent.

The aqueous diluent is preferably selected from the group consisting of water and mixtures of water with physiologically-tolerable solvents. The physiologically-tolerable solvents are organic solvents preferably selected from the group consisting of $C_{1-6}$ alcohols (in particular ethanol), polyethylene glycol, propylene glycol, glycerol, dimethylacetamide, dimethyl isosorbide, dimethyl sulfoxide, 1-methyl-2-pyrrolidone and 1-ethyl-2-pyrrolidone. The solvents are usually liquid at room temperature (20° C.).

Preferably, the polyethylene glycol is selected from the group of parenterally-injectable polyethylene glycols, in particular PEG 300, PEG 400 and PEG 600. In the aforementioned nomenclature, "PEG" designates "polyethylene glycol" and the number reflects the average relative molecular mass.

In a preferred embodiment, the polyethylene glycol is selected from polyethylene glycols having an average relative molecular mass ranging from 200 to 700, more preferably from 300 to 600 and especially from 350 to 550.

The aqueous diluents may further comprise additional compounds such as salts, preferably selected from sodium, magnesium, calcium, potassium, chloride, lactate, acetate, malate, gluconate, citrate and bicarbonate; and/or polyols such as glucose, mannitol, sucrose, trehalose, sorbitol.

The kit according to the disclosure allows on-site preparation of the aqueous composition of the disclosure in a form suitable for injection. The amount of the powder of the disclosure comprised in the at least one first compartment and the amount of water of aqueous diluents comprised in the at least one second compartment are preferably matched to each other such to allow complete dissolution of the inventive powder.

The first and the second compartment are preferably separate from each other, preferably physically separated from each other, e.g. separated by a wall or foil.

In a preferred embodiment, the kit according to the disclosure is in the form of a bag, cartridge, container, vial, syringe or bottle.

In a preferred embodiment, the kit is in the form of a bag comprising the first and the second compartment which are separated from each other, for example by means of a partition wall.

The material of the kit is preferably chemically inert and does not react with the contents. Further preferred is a material that additionally protects the contents of the compartments against any form of exposure that may result in the decomposition of the contents, e.g. heat and/or light. Preferably, the material is selected from the group consisting of glass, organic polymers and mixtures thereof. Further preferred is a kit of the disclosure wherein said kit or at least the first and/or at least the second compartment is/are made of a material selected from the group consisting of glass, organic polymers and mixtures thereof. Preferred organic polymers are polyethylene and/or polypropylene.

Preferably, the kit can be sealed to avoid contamination of the contents by, for example, bacteria or other microbes.

In a preferred embodiment of the kit, the compartments are arranged in such a way as to prevent unintentional mixing of the contents.

A further object of the present disclosure is a method for the preparation of the aqueous composition of the disclosure. The method comprises the steps of dissolving components (A) and (B) in an aqueous diluent and adjusting the pH of the solution to greater than 7.

In a preferred embodiment, the method comprises the following steps:
a) Dissolving component (A) and component (B) in an aqueous diluent to obtain an aqueous solution of component (A) and component (B) in a molar ratio of from 1:2 to 1:30, preferably 1:3 to 1:30;
b) Optionally adjusting the pH of the aqueous solution of step a) to greater than 7, preferably in the range of 7.5 to 10.5;
c) Lyophilization of the aqueous solution obtained in step a) or b) to obtain a dried powder;
d) Reconstituting the powder of step c) in an aqueous diluent.

A further object of the present disclosure is a pharmaceutical formulation comprising the composition of the disclosure or the powder of the disclosure.

A further aspect of the disclosure is a formulation for use as a medicament, which either (i) comprises or consists of the aqueous composition of the disclosure; or (ii) comprises or consists of the powder of the present disclosure.

The formulation according to the disclosure may further comprise other pharmaceutical excipients and/or adjuvants, such as crystallization retarding agents, antioxidants and fats. The total amount of each member of the list consisting of crystallization retarding agents and antioxidants is usually lower than 10 wt.-%, preferably lower than 3 wt.-%, more preferably lower than 1 wt.-%, especially lower than 0.1 wt.-%, in particular lower than 0.01 wt.-%, based on the total amount of the formulation. The excipients are preferably chosen to allow a safe and accurate administration. In a preferred embodiment, the crystallization retarding agent is polyvinyl pyrrolidone (PVP). Preferred is a PVP with an average molecular weight ranging from 2000 to 11000. Especially preferred is Povidone K12 having an average molecular weight of about 2500 or Povidone K17 having an average molecular weight of about 10000.

In a preferred embodiment, the formulation of the disclosure or the aqueous composition of the disclosure further comprises an osmolality agent.

Preferably, the osmolality agent is an isoosmolality agent or an isotonic agent, preferably a nonionic isotonic agent.

In a further preferred embodiment, the osmolality agent is an aliphatic polyhydroxy alkanol having 2 to 10 carbon atoms, preferably selected from the group consisting of mannitol, fructose, glucose, gluconolactone, gluconate, sucrose, lactose, trehalose, dextrose, dextran, hydroxyethyl starches and mixtures thereof.

Further preferred osmolality agents are selected from the group consisting of glycine gelatin, calcium gluconoglucoheptonate, potassium chloride, calcium chloride, sodium chloride and mixtures thereof.

Preferably, the osmolality agent is present in an amount ranging from 0.5 to 10 percent by weight, more preferably from 1 to 7 percent by weight, still more preferably from 1.5 to 5 percent by weight and especially from 2 to 4 percent by weight. The amounts referred to are based on the total weight of the formulation or the aqueous composition.

The preferred osmolality of the formulation according to the disclosure ranges from 250 mOsm/kg to 600 mOsm/kg, more preferably from 280 mOsm/kg to 450 mOsm/kg.

In a preferred embodiment, the formulation or aqueous composition of the disclosure comprises or is consisting of
 component (A) in an amount ranging from 0.75 mmol/l to 15.0 mmol/l;
 component (B) in an amount ranging from 5.0 mmol/l to 250.0 mmol/l;
 an aqueous diluent;
 optionally a pH adjuster in an amount ranging from 0.2 mmol/l to 20.0 mmol/l; and
 optionally an osmolality agent in an amount ranging from 25.0 mmol/l to 250.0 mmol/l, wherein the concentrations are based on the total volume of the formulation or aqueous composition, and wherein the molar ratio of component (A) to component (B) ranges from 1:2 to 1:30, preferably 1:3 to 1:30.

In a preferred embodiment, the formulation or the aqueous composition of the disclosure is injectable and comprises or is consisting of
 dantrolene sodium salt in a concentration ranging from 1.5 to 15 mg/ml, preferably from 1.6 toll mg/ml;
 2-hydroxypropyl-β-cyclodextrin in a concentration ranging from 75 to 350 mg/ml, preferably from 80 to 320 mg/ml;
 an aqueous diluent;
 optionally a pH adjuster in a concentration of up to 25 mmol/l, preferably from 0.1 to 20 mmol/l; and
 optionally an osmolality agent in a concentration of up to 200 mmol/l, preferably from 20 to 200 mmol/l, wherein the aqueous diluent consist of water or a mixture of water with a physiologically tolerable solutent, and wherein the molar ratio of component (A) to component (B) ranges from 1:2 to 1:30, preferably 1:3 to 1:30.

The dosage regime in which the inventive formulation may be administered depends on the individual circumstances of each patient and has to be carefully considered for each case. Preferably, the recommended dosage regime ranges from 1 mg/kg per day to 10 mg/kg per day, preferably 1.5 mg/kg per day to 3.0 mg/kg per day, the kg referring to the body weight of the individual patient and the mg quantity referring to the quantity of component (A).

Dantrolene or its pharmaceutically acceptable salts is/are known to lessen the excitation-contraction-coupling in muscle cells. A further object of the present disclosure is therefore a pharmaceutical formulation of the disclosure for use as a muscle relaxant. Preferably, the pharmaceutical formulation according to the disclosure is for use in the treatment of diseases related to muscular cramps, in particular plasticity following a stroke. In an especially preferred embodiment, the pharmaceutical formulation according to the disclosure is for use in the treatment of malignant hyperthermia.

In order to treat a disease as effectively as possible, it is important that the respective drug is administered in a way to ensure high target specificity and fast uptake at the site of action. The pharmaceutical formulation according to the disclosure is therefore preferably administered parenterally, in particular intravenously.

A further object of the present disclosure is a method for the treatment of pathological conditions related to muscle cramps which comprises administering the aqueous composition of the disclosure or the pharmaceutical formulation of the disclosure. In a preferred embodiment, the administration is parenteral, preferably intravenous.

The aqueous composition and the pharmaceutical formulations of the present disclosure are injectable. This means that aqueous composition and the pharmaceutical formulation is safe for injection.

We define "safe for injection" to mean a formulation that can be reliably injected intravenously into appropriate test subjects or model mammals, at relevant clinical doses, with a low incidence of life-threatening complications due to the formulation, where low incidence means less than about 10% of cases, and preferably less than about 1% of cases. In particular, formulation-related toxicities, such as pulmonary emboli (PE) due to supermicron-sized particles or aggregates, pathologically altered arterial pressures, or severe vascular damage, must be limited to low incidence. It is important to point out that in the context of the current patent, the term "safe for injection" does not in any way imply a restriction of a drug formulation to intravenous injection, it merely means that the formulation is sufficiently safe so as to allow intravenous injection. The reason for focusing on the intravenous route with regard to the safety issue is that even when a formulation is administered by another route of injection, such as intramuscular, intraarterial, subcutaneous, intraperitoneal, intraocular, or by local instillation, the danger of inadvertent routing to a vein cannot be ignored, and often demands that the formulation be safe even if errant administration results in what is essentially an intravenous administration. Because of this, in this patent we use the terms "safe for intravenous injection" and "safe for injection" interchangeably.

Another aspect of this disclosure centers around a class of new indications for the use of the dantrolene or a dantrolene salt. In particular, it is an object of this disclosure to provide a method by which to prevent, reduce or reverse the negative cerebrospinal and cognitive injuries, described herein, which can be associated with altered, and especially decreased, blood pressures; altered, and especially decreased, blood flow; altered, and especially decreased cerebral perfusion; altered, and especially diminished pulsatile flow, as well as increased intracranial pressures which inherently alter, and especially impair cerebral perfusion and subsequent oxygenation of cerebral tissues; and non-normothermic states especially those which are sustained for more than about four hours. The phenomena of altered cognitive abilities and function as well as neuropsychiatric changes with or without impaired motor function is commonly referred to as "pumphead" among anesthesiologists, cardiothoracic surgeons, and certain other medical personnel. In particular, in this disclosure, it is envisioned that the prophylactic administration of dantrolene, or one of its salts, analogs or relatives, may prevent or limit the effects of these neurological complications via a unique and synergistic combination of a number of intracellular and/or metabolic mechanisms, and via stabilization of intracellular calcium. It is further expected that dantrolene will be a suitable treatment agent capable of minimizing neurological complications when provided in a manner timely to the insult, not only in humans but potentially in veterinary settings as well.

In addition, another aspect of the disclosure are new indications for dantrolene or dantrolene salts, for which existing dantrolene formulations as well as low-volume formulations as disclosed herein provide for a new method of treatment and prophylaxis. The inventors have recognized that dantrolene or dantrolene salts provide a surprising and synergistic combination of biochemical and pharmacologic mechanisms that make it of unique applicability in the prevention and treatment of certain cerebrospinal, and especially cognitive, injuries which prior to this disclosure were poorly treated. Attention to such injuries, particularly when their symptomology is "silent", and sometimes delayed, following in the aftermath of certain surgical procedures, has in previous medical practice taken a back seat to the primary surgical indication.

In the following non-exhaustive list of some of the advantages of the present disclosure, in addition to those already mentioned, are given:
- a surprisingly high amount of dantrolene (salts) can be dissolved, especially a significantly higher concentration of dantrolene (salts) in the solution than was possible with the prior art can be reached,
- clear solutions can be obtained that can be easily filtered,
- sterile powder formulations can be obtained from the clear and filtered liquid solutions of component (A),
- the powder formulations show a fast reconstitution time leading to a parenteral solution that is clear and free of particulate matters and can be injected immediately,
- the preparations reconstituted from the powder formulations meet the regulatory requirements in view of the regulatory turbidity limits (the European Phamacopoeia sets the limit of the turbidity value to NTU=3),
- the solutions of dantrolene (salts) show very good stability and are readily parenterally-injectable,
- the preparations are able to solubilize much higher amounts of dantrolene (salts), both in initial solutions as well as in reconstituted solutions,
- a large(r) quantity of active ingredient can be injected in less time when the preparations of the present disclosure (solution as well as powder) are being used—the time needed to reach the therapeutic dose is drastically shortened,
- an increase of the bioavailability of dantrolene (salts) is clearly anticipated.

BRIEF DESCRIPTION OF THE DRAWING FIGURES

The foregoing summary and the following description will be better understood when reviewed in connection with the drawing figures, of which.

DETAILED DESCRIPTION

The present disclosure is illustrated in more detail through the following examples:

Table 1 summarizes the contents of exemplary compositions according to the disclosure, wherein the aqueous diluent is water and wherein the concentrations are based on the total volume of the composition.

TABLE 1

|  | Example 1 | Example 2 | Example 3 | Example 4 |
| --- | --- | --- | --- | --- |
| Dantrolene sodium salt (mg/ml) | 1.7 | 3.3 | 6.7 | 10.0 |
| HP-β-CD* (mg/ml) | 83.3 | 133.3 | 266.6 | 300.0 |
| pH adjuster (mmol/l) | 1.0 | 0.0 | 20.0 | 0.0 |
| Osmolality agent (mmol/l) | 0.0 | 180.0 | 0.0 | 0.0 |
| pH after reconstitution | 8.5 | 9.0 | 8.9 | 10.0 |

*2-hydroxypropyl-β-cyclodextrin; molar substitution 0.6

The compositions were prepared by dissolving and thoroughly mixing the appropriate amounts of dantrolene sodium salt, 2-hydroxypropyl-β-cyclodextrin (HP-β-CD) and pH adjuster in water. The obtained mixture was lyophilized to obtain a dried powder. The powder was then reconstituted in water for injection or an aqueous solution comprising 5 wt.-% dextrose and the pH of the newly obtained solution determined.

Experiments were conducted using different components (B) and varying the pH of the composition.

In these experiments four different cyclodextrins were tested in combination with dantrolene sodium salt. The concentration of the cyclodextrin compound was 50 mg/ml and the concentration of dantrolene sodium salt was 1 mg/ml. The pH values were adjusted by using a buffer composed of phosphate 25 mM and Tromethamine 25 mM in water to reach pH 6.0, 7.0, 8.0, 9.0 and 10.0, respectively. The obtained solutions were stored at room temperature and examined over the course of 10 days. The solubility of dantrolene sodium salt was determined after 24 and 48 hours. The solutions were analyzed by visual observation, whilst the content of the dantrolene sodium salt and the degradation profile were determined by HPLC and pH value monitoring.

Dantrolene content and degradation profiles were determined on an Agilent Series 1100 HPLC equipment (Agilent Technologies Inc, Santa Clara, CA, USA) fitted with a quaternary pump, an autosampler, a diode-array detector and a thermostated column compartment. Samples were analyzed on a Kinetex XB-C18 column (75×4.6 mm, 2.6 μm, Phenomenex) with mobile phases consisting of water with 0.1% formic acid (A) and acetonitrile with 0.1% formic acid (B) using a linear gradient from 15% to 45% (B) in 12 minutes.

pH measurements were performed using a Metrohm pH mobile 826 (Metrohm SA, Herisau, Switzerland) equipped with a glass pH electrode. Unless stated otherwise measurements have been performed at 20° C.

The following cyclodextrins were tested:

A: control (phosphate/tromethamine solution)
B: β-cyclodextrin (CAS [7585-39-9])
F: Sulfobutylether-β-cyclodextrin sodium salt (degree of substitution 6.0-7.1; CAS [182410-00-0])
D: 2-hydroxyethyl-3-cyclodextrin (molar substitution 0.7; CAS [128446-32-2])
E: 2-hydroxypropyl-β-cyclodextrin (molar substitution 0.6; CAS [12446-35-5])

FIGS. 1 to 5 depict the results of the solubility measurements at pH values of 6.0 (FIG. 1), 7.0 (FIG. 2), 8.0 (FIG. 3), 9.0 (FIG. 4), and 10.0 (FIG. 5), respectively. As can be seen from the Figures, solubility was enhanced in all cases and further increased with increasing pH. The best results were obtained when compound (B) was 2-hydropropyl-β-cyclodextrin, with almost complete solubility of the dantrolene salt being achieved at pH 9. The improved solubility could be maintained over an extended period of time, i.e. the precipitation of dantrolene sodium usually seen with compositions in the art was not observed in the case of the compositions according to the disclosure.

FIGS. 6 to 10 show the degradation profile of dantrolene sodium in the tested solutions over a period of 10 days at pH values of 6.0 (FIG. 6), 7.0 (FIG. 7), 8.0 (FIG. 8), 9.0 (FIG. 9), and 10.0 (FIG. 10), respectively. As is confirmed by the data, the solutions according to the disclosure are even at higher pH values, stable and only slight degradation is observed towards the end of the ten-day-period.

The improved stability of the inventive compositions is further demonstrated by the data shown in Table 2. Table 2 depicts the effect of 2-hydroxypropyl-β-cyclodextrin on the stability of dantrolene sodium at pH 9 (Solution 1) versus a solution which does not contain 2-hydroxypropyl-β-cyclodextrin (Solution 3). As can be seen, almost no loss of content (i.e. no precipitation of dantrolene free acid) of the dantrolene salt could be observed whereas rapid loss of content took place in the absence of 2-hydroxypropyl-β-cyclodextrin.

TABLE 2

| Time (day) | Solution 1 amount of dantrolene sodium salt (%) | Solution 2 amount of dantrolene sodium salt (%) | Solution 3 (comp.)[1] amount of dantrolene sodium salt (%) | Solution 4 (comp.)[2] amount of dantrolene sodium salt (%) | Solution 5 (comp)[3] amount of dantrolene sodium salt (%) |
|---|---|---|---|---|---|
| 0 | n.m. | 100.0 | n.m. | n.m. | 100.0 |
| 1 | 100.0 | 97.3 | 100.0 | 100.0 | 51.4 |
| 2 | 99.2 | n.m. | 78.7 | 64.4 | n.m. |
| 6 | 96.0 | n.m. | 69.7 | 47.1 | n.m. |
| 8 | n.m. | 89.7 | n.m. | n.m. | 42.6 |
| 10 | 97.0 | n.m. | 29.7 | 40.3 | n.m. |
| 11 | n.m. | 88.0 | n.m. | n.m. | 39.1 | n.m. = not measured
[1] comparative - without cyclodextrin
[2] comparative with A.C.A. Jansen et al., International Journal of Pharmaceutics, 75 (1991) 193-199
[3] comparative; process as in WO 2010/126818, example 3

The solutions were prepared as follows:

Solution 1
10 mg of Dantrolene sodium salt were added to 10 ml of a 50 mg/ml 2-hydroxypropyl-β-cyclodextrin solution prepared in a phosphate/tromethamine buffer (25 mM/25 mM) adjusted to pH 9 in water. Molar ratio of dantrolene sodium to 2-hydroxypropyl-beta-cylodextrion about 1:15 (Molecular weight of dantrolene sodium M=399.33 g/mol and of 2-hydroxypropyl-beta-cylodextrin M=1400 g/mol).

Weight ratio of dantrolene sodium to 2-hydroxypropyl-beta-cyclodextrin 1:50.

Solution 2
Prepared as in example 1; weight ratio of dantrolene sodium to 2-hydroxypropyl-beta-cyclodextrin 1:10.

Solution 3—Control Solution without Cyclodextrin
10 mg of Dantrolene sodium salt were added to 10 ml of a phosphate/tromethamine buffer solution (25 mM/25 mM) adjusted to pH 9.

Solution 4—Comparative Prepared as solution 1 but using unsubstituted cyclodextrin (i.e. β-cyclodextrin).

Solution 5—Comparative
Prepared as described in WO 2010/126818, example 3 but with ratio (w/w) of dantrolene: 2-hydroxypropyl-beta-cylodextrin=2.5:

At each time, the solution was filtered and the content of dantrolene sodium salt determined by HPLC.

As can be seen form Table 2, compositions of the present disclosure show, inter alia, improved stability with respect to the prior art.

Figure 1:
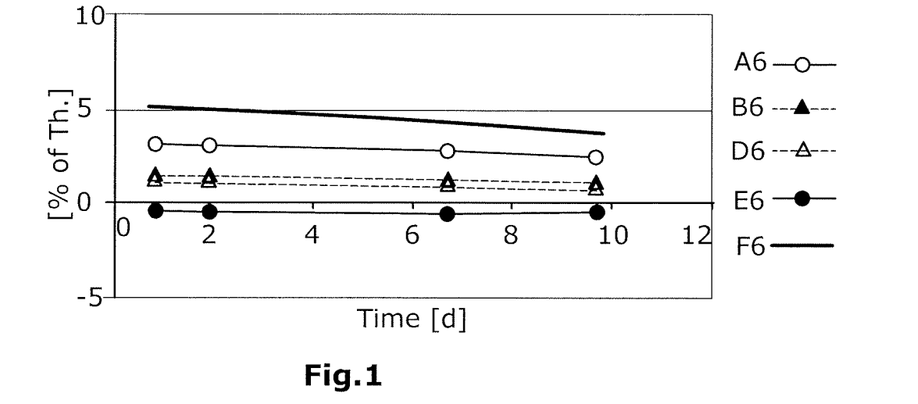
FIG. 1 is a graph depicting results of solubility measurements at a pH value of 6.0.
Figure 2:
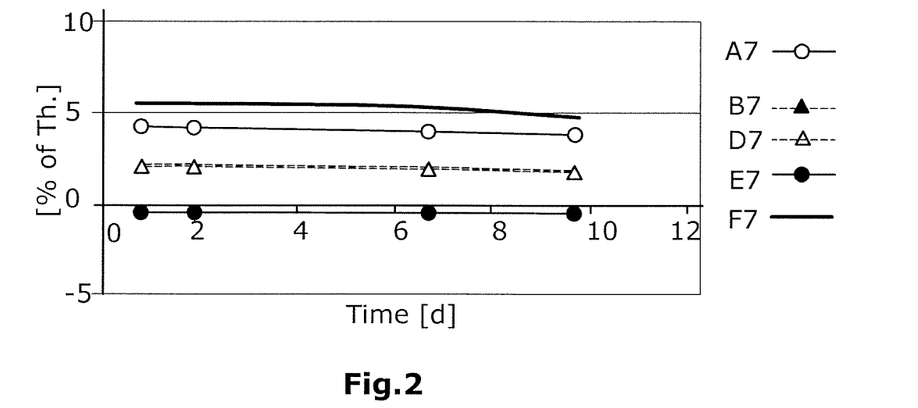
FIG. 2 is a graph depicting results of solubility measurements at a pH value of 7.0.
Figure 3:
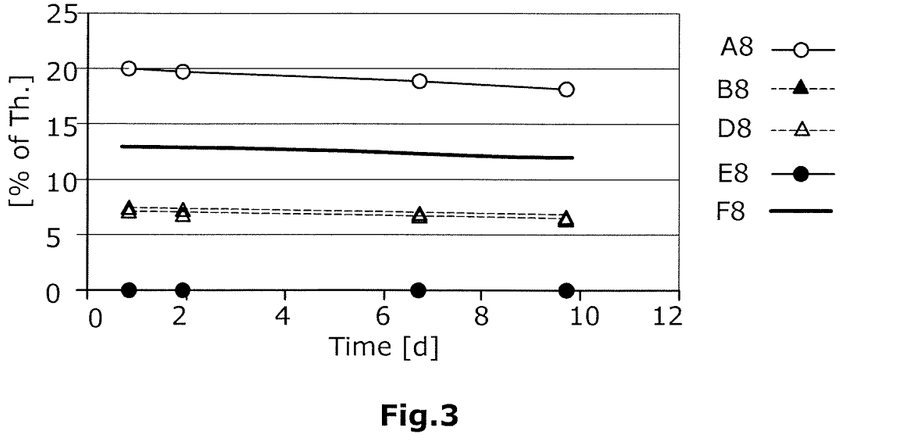
FIG. 3 is a graph depicting results of solubility measurements at a pH value of 8.0.
Figure 4:
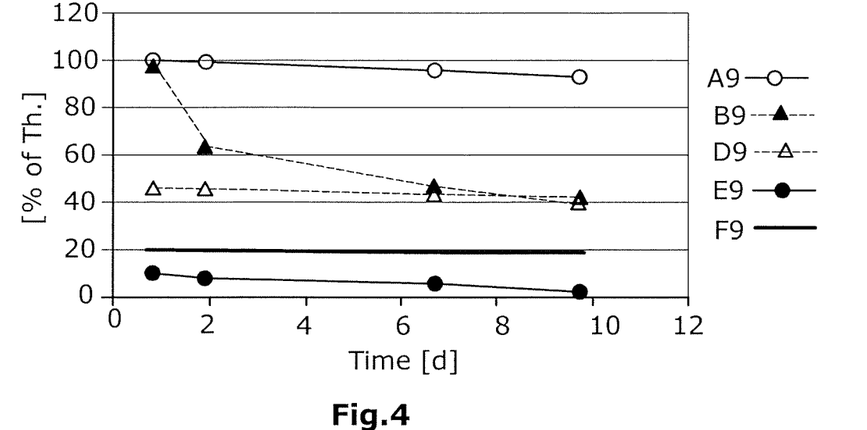
FIG. 4 is a graph depicting results of solubility measurements at a pH value of 9.0.
Figure 5:
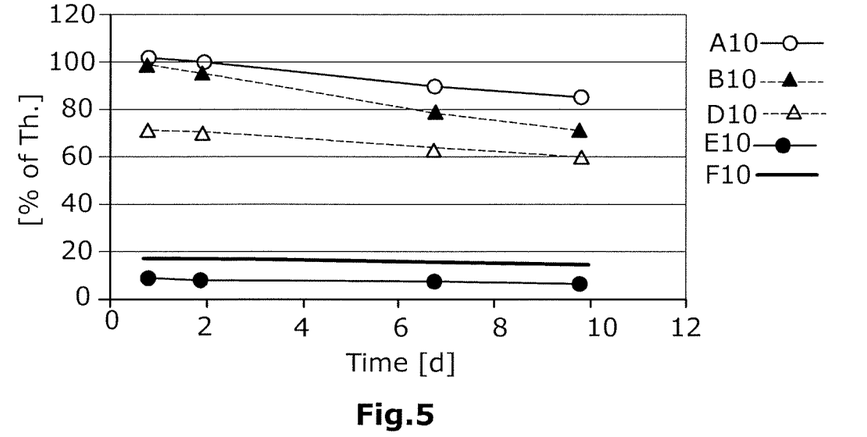
FIG. 5 is a graph depicting results of solubility measurements at a pH value of 10.0.
Figure 6:
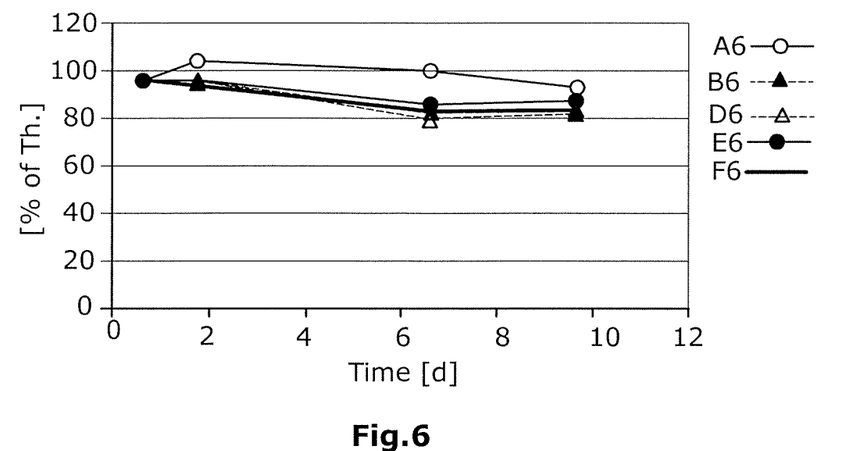
FIG. 6 is a graph depicting the degradation profile of dantrolene sodium at a pH value of 6.0.
Figure 7:
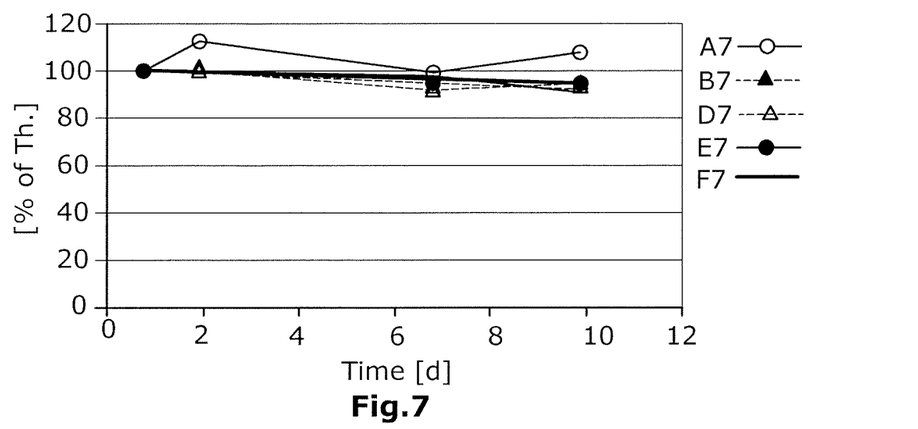
FIG. 7 is a graph depicting the degradation profile of dantrolene sodium at a pH value of 7.0.
Figure 8:
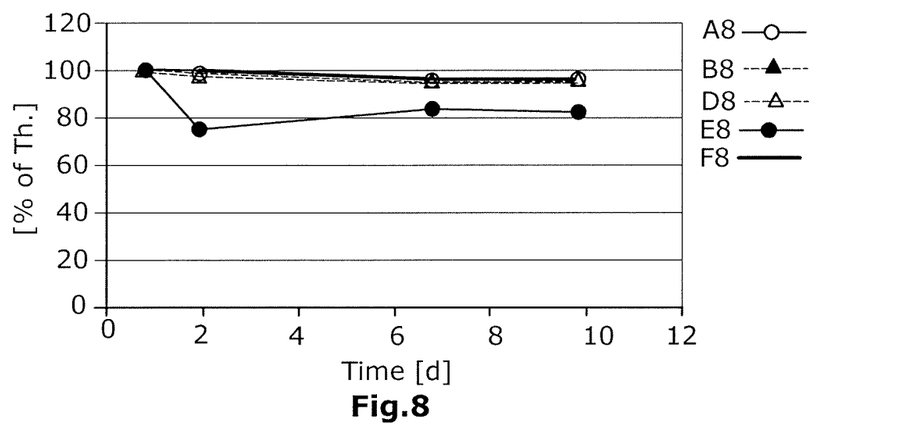
FIG. 8 is a graph depicting the degradation profile of dantrolene sodium at a pH value of 8.0.
Figure 9:
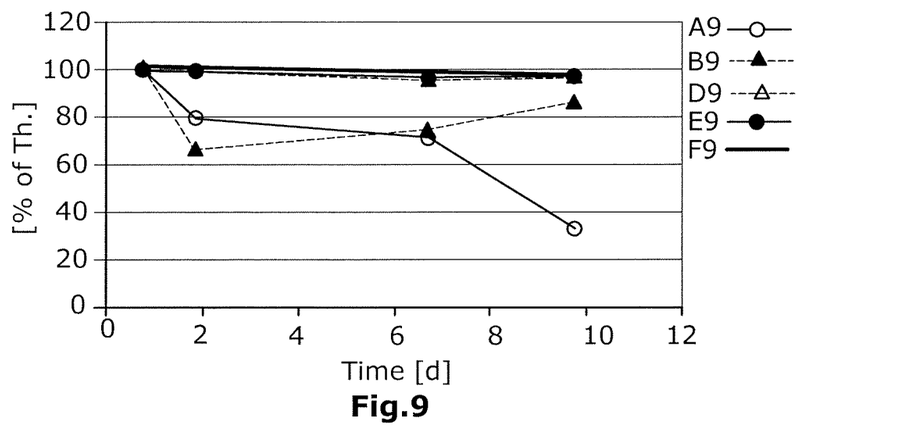
FIG. 9 is a graph depicting the degradation profile of dantrolene sodium at a pH value of 9.0.
Figure 10:
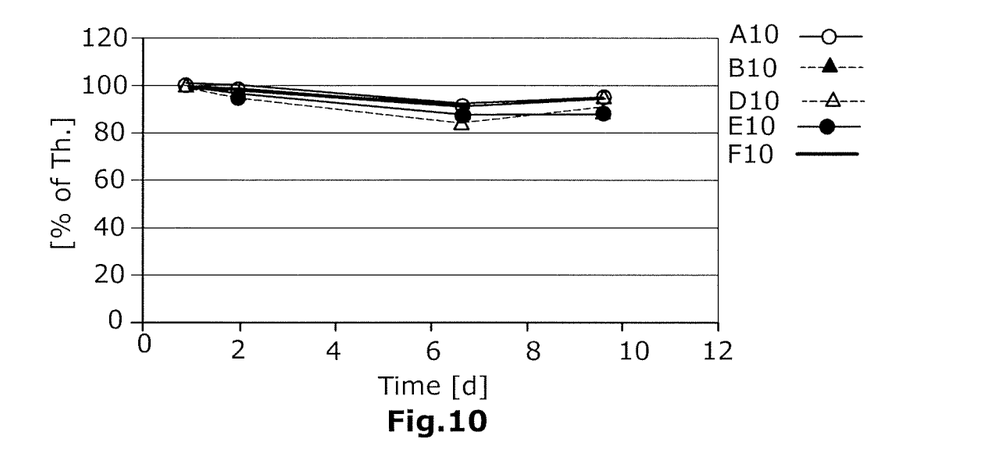
FIG. 10 is a graph depicting the degradation profile of dantrolene sodium at a pH value of 10.0.
Figure 11:
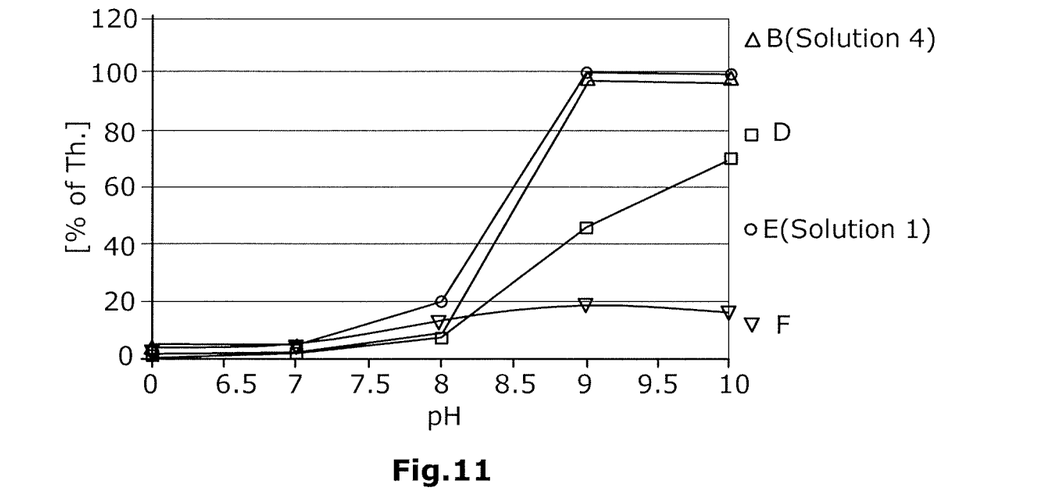
FIG. 11 shows the correlation between the solubility of dantrolene sodium salt and pH after one day.
Figure 12:
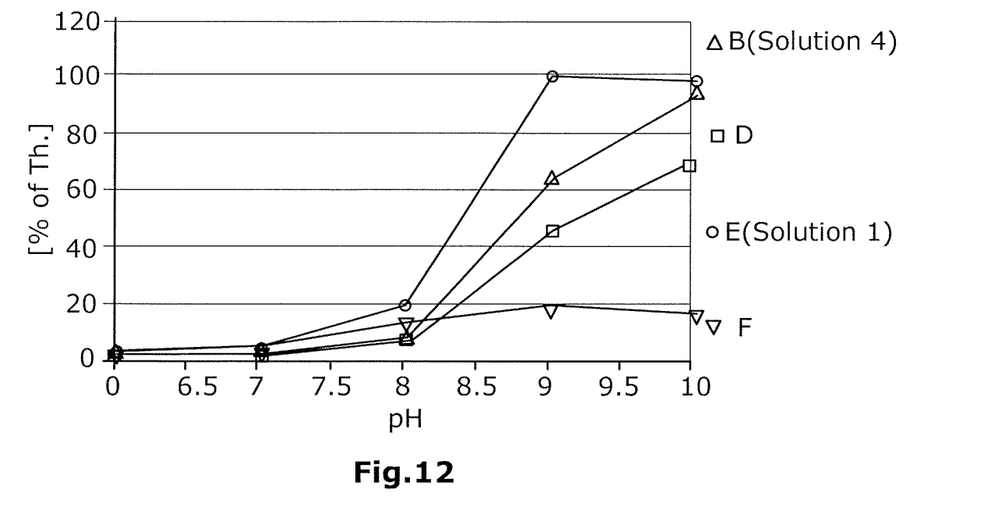
FIG. 12 shows the correlation between the solubility of dantrolene sodium salt and pH after two days.

FIGS. 11 and 12 refer to the correlation between the solubility of dantrolene sodium salt and the pH of the solution. FIG. 11 depicts the data obtained from measuring the solubility of the dantrolene compound after one day whereas the data summarized in FIG. 12 was obtained after two days. As can be seen, the solubility of dantrolene sodium salt increases with increasing pH, whereby the best results were achieved when 2-hydroxypropyl-β-cyclodextrin was also used.

Figure 13:
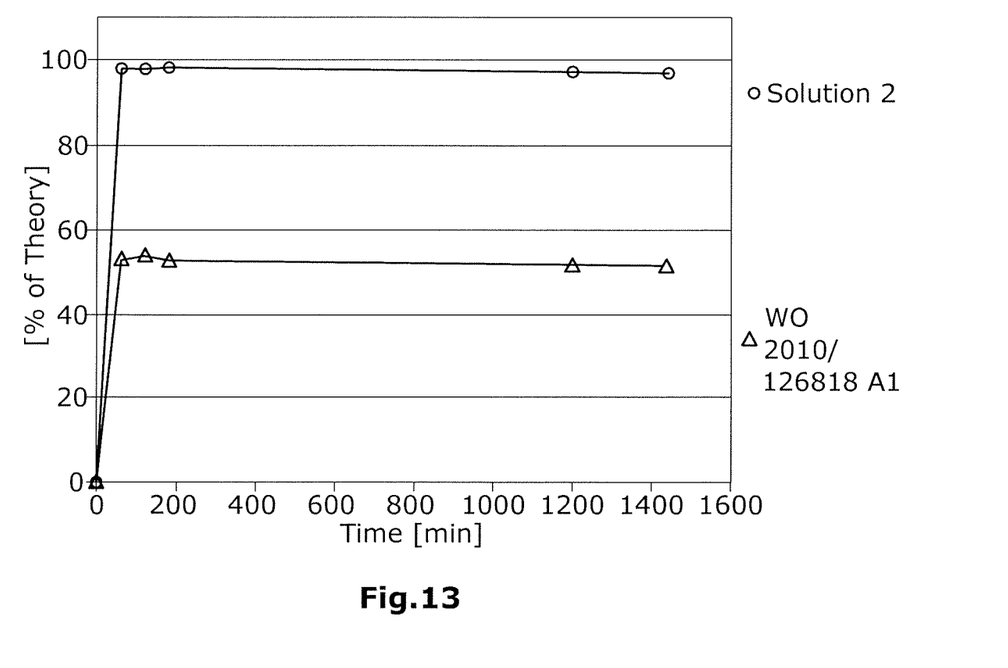
FIG. 13 is a graph comparing solubility of powder prepared from a formulation of the present disclosure with a known formulation.

Further, inventive powders obtained by freeze-drying the above solution 2 have been compared with those of WO 2010/126818 A1. As can be seen from FIG. 13, the preparation of the present disclosure is able to solubilize a higher amount (+100%) of the sodium dantrolene due to the particular ratio of component (A) to component (B) compared with the formulation according to WO 2010/126818 A1.

Indeed much more dantrolene is solubilized in the reconstituted solution meaning that a larger quantity of active ingredient can be injected in less time. In other words, the time needed to reach the therapeutic dose is drastically shortened. Also an increase of the bioavailability in the context of this example is projected. This attribute is more than ever important and critical for patients suffering of malignant hyperthermy due to the emergency situation. A further difference (not depicted in FIG. 13) is that the preparations of the present disclosure are clear solutions while those of WO 2010/126818 A1 are not even solutions at all but turbid, heterogeneous mixtures.

Figure 14:
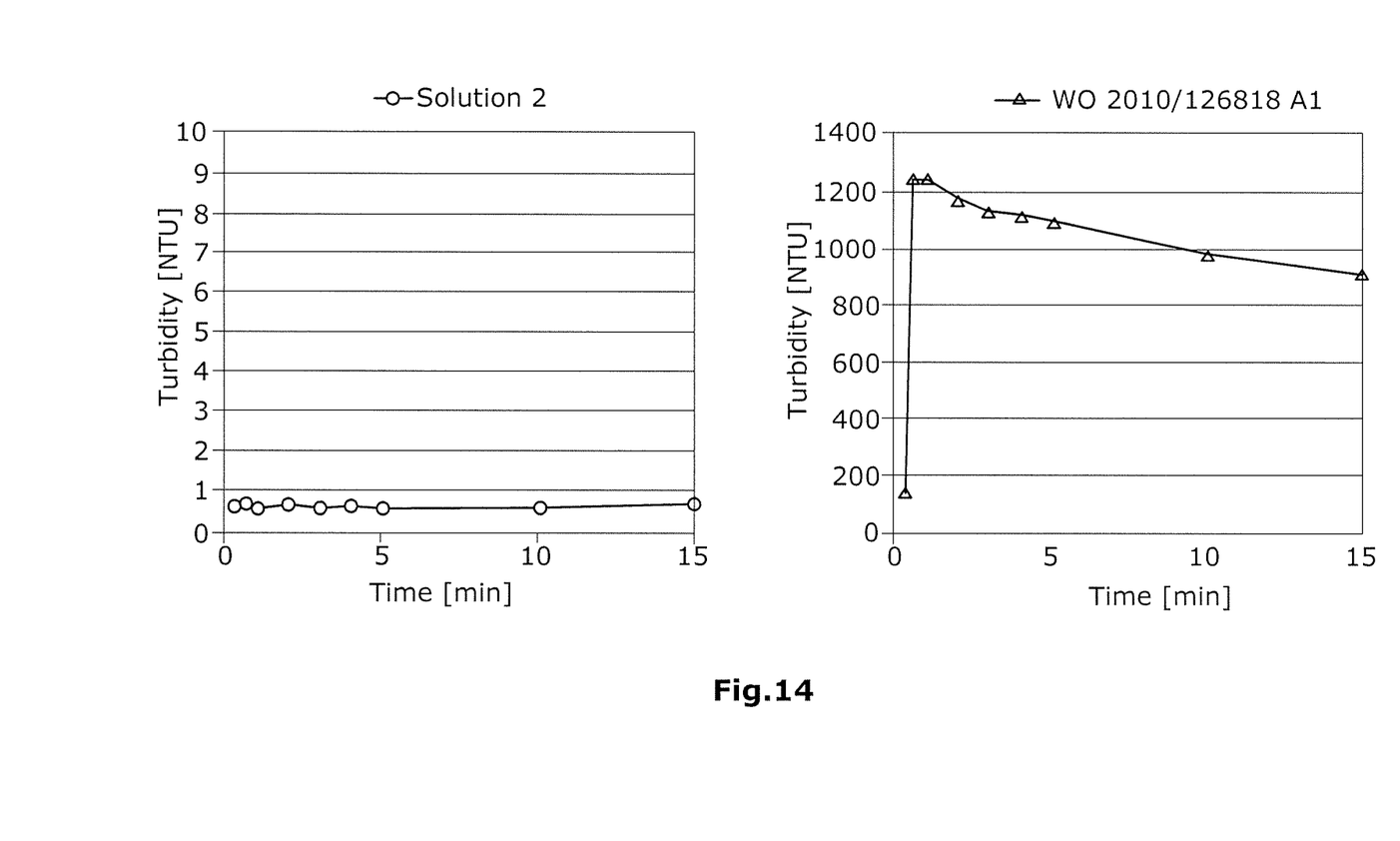
FIG. 14 is a graph comparing turbidity values of preparations according to the present disclosure with turbidity values of a known formulation.

Also the powder formulations according to the present disclosure show a fast reconstitution time leading to a parenteral solution that is clear and free of particulate matters and can be injected immediately. Whereas the preparations according to WO 2010/126818 A1 are very turbid with visible particles after their reconstitution. The preparations of WO 2010/126818 A1 have turbidity values 1000 times more turbid (opalescent) compared to the regulatory limit (NTU=3) for a parenteral product (FIG. 14). Accordingly with the present disclosure the regulatory limits are met, but not with preparations according to WO 2010/126818 A1.

The powders according to the present disclosure could be obtained in a sterile way, because they stem from a clear and filtered liquid solution of dantrolene sodium, while the preparations of WO 2010/126818 A1 cannot be sterilized by filtration due to the heterogeneous form of the suspension formulation. This is because of the difference in preparation; according to the present disclosure component (A) is dissolved (i.e. resulting in a clear solution) while the preparations of WO 2010/126818 A1 are prepared with a kneading process resulting in a paste.

In summary, the present disclosure provides an aqueous dantrolene solution which not only shows improved solubility but also increased stability, in particular in an alkaline environment. The best results were obtained in a pH range of 8 to 9, thus demonstrating that the degradation of dantrolene salts at higher pH can be avoided.

The invention claimed is:

1. An aqueous composition, comprising:
   i) a component (A) selected from one or more members of the group consisting of dantrolene and a pharmaceutically acceptable salt of dantrolene; and
   ii) a component (B) selected from one or more members of the group consisting of 2-hydroxyethyl-β-cyclodextrin, sulfobutylether-β-cyclodextrin and 2-hydroxypropyl-β-cyclodextrin,
   wherein a pH of the composition is between 8.5 and 9.5,
   wherein a molar ratio of component (A) to component (B) ranges from 1:7 to 1:20, and
   wherein at least 90% of component (A) remains soluble for at least two days.

2. The aqueous composition according to claim 1, wherein the molar ratio of component (A) to component (B) ranges from 1:10 to 1:15.

3. The aqueous composition according to claim 1, wherein the pH of the aqueous composition is about 9.

4. The aqueous composition according to claim 1, wherein component (B) has a molar substitution (MS) ranging from 0.05 to 10.

5. The aqueous composition according to claim 1, further comprising a pH adjuster.

6. The aqueous composition according to claim 5, wherein the molar ratio of component (A) to the pH adjuster is 20:1 to 1:20.

7. The aqueous composition according to claim 1, further comprising an osmolality agent.

8. The aqueous composition of claim 1, wherein at least 90% of component (A) remains soluble after ten days.

9. The aqueous composition of claim 1, wherein component (B) is sulfobutylether-β-cyclodextrin.

10. The aqueous composition of claim 1, wherein component (B) is 2-hydroxypropyl-β-cyclodextrin.

11. An aqueous composition, comprising:
    i) a component (A) selected from one or more members of the group consisting of dantrolene and a pharmaceutically acceptable salt of dantrolene; and
    ii) a component (B) selected from one or more members of the group consisting of cyclodextrin derivatives comprising one or more substituents,
    wherein a molar ratio of component (A) to component (B) ranges from 1:2 to 1:30, and
    wherein component (A) remains soluble at concentrations up to 10 mg/mL.

12. The aqueous composition according to claim 11, wherein the molar ratio of component (A) to component (B) ranges from 1:2 to 1:20.

13. The aqueous composition according to claim 11, wherein the molar ratio of component (A) to component (B) is 1:10.

14. The aqueous composition according to claim 11, wherein the molar ratio of component (A) to component (B) is 1:11.

15. The aqueous composition according to claim 11, wherein component (B) is 2-hydroxypropyl-β-cyclodextrin.

16. The aqueous composition according to claim 11, wherein the pH of the aqueous composition is between 8.5 to 9.5.

17. A method of treating a patient with malignant hyperthermia or in need of muscle relaxation, comprising: intravenously administering to the patient with an effective amount of an aqueous composition comprising:
    a component (A) selected from one or more members of the group consisting of dantrolene and a pharmaceutically acceptable salt of dantrolene; and
    a component (B) selected from one or more members of the group consisting of cyclodextrin derivatives,
    wherein a pH of the composition is greater than 7, and
    wherein a molar ratio of component (A) to component (B) ranges from 1:2 to 1:30.

18. A composition comprising:
    a component (A), dantrolene or a pharmaceutically acceptable salt thereof; and
    a component (B), a β-cyclodextrin, or derivative thereof;
    an aqueous dilutant; and
    wherein:
    a pH of the composition is from 8.0 to 10.0;
    a molar ratio of component (A) to component (B) ranges from 1:3 to 1:15; and
    the dantrolene is dissolved in the aqueous dilutant.

19. The composition of claim 18, wherein the β-cyclodextrin is 2-hydroxypropyl-β-cyclodextrin.

20. The composition of claim 19, wherein component (A) is dantrolene sodium.

21. The composition of claim 20, wherein component (A) is present in a concentration ranging from 0.1 to 10 mg/ml.

22. The composition of claim 21, wherein component (B) is present in a concentration ranging 50 to 300 mg/ml.

23. The composition of claim 22, wherein the aqueous dilutant is a mixture of water with a physiologically-tolerable solvent.

24. The composition of claim 23, wherein the water is higher than 50 wt-%.

25. The composition of claim 24, wherein the physiologically-tolerable solvent is selected from the group consisting of a $C_{1-6}$ alcohol, a polyethylene glycol, a propylene glycol, a glycerol, a dimethylacetamide, a dimethyl isosorbide, a dimethyl sulfoxide, a 1-methyl-2-pyrrolidone and a 1-ethyl-2-pyrrolidone.

26. The composition of claim 25, wherein the physiologically-tolerable solvent is a polyethylene glycol.

27. The composition of claim 26, wherein component (B) has a molar substitution ranging from 0.2 to 0.9.

28. The composition of claim 27, further comprising a pH adjuster.

29. The composition of claim 28, wherein the molar ratio of component (A) to the pH adjuster is 20:1 to 1:20.

30. The composition of claim 29, further comprising an osmolality agent.

31. The composition of claim 30, wherein the osmolality agent is present in an amount ranging from 0.5 to 10 percent by weight based on the total weight of the aqueous composition.

\* \* \* \* \*

UNITED STATES PATENT AND TRADEMARK OFFICE
CERTIFICATE OF CORRECTION

| | | |
|---|---|---|
| PATENT NO. | : 11,844,782 B2 | Page 1 of 1 |
| APPLICATION NO. | : 15/952477 | |
| DATED | : December 19, 2023 | |
| INVENTOR(S) | : Schwebel et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 420 days.

Signed and Sealed this
First Day of July, 2025

Coke Morgan Stewart
*Acting Director of the United States Patent and Trademark Office*